United States Patent
Bathe et al.

(10) Patent No.: US 7,252,977 B2
(45) Date of Patent: Aug. 7, 2007

(54) NUCLEOTIDE SEQUENCES WHICH CODE FOR THE MSIK GENE

(75) Inventors: Brigitte Bathe, Salzkotten (DE); Natalie Schischka, Bielefeld (DE); Mike Farwick, Bielefeld (DE); Walter Pfefferle, Halle (DE)

(73) Assignee: Degussa AG, Dusseldorf (DE)

( * ) Notice: Subject to any disclaimer, the term of this patent is extended or adjusted under 35 U.S.C. 154(b) by 166 days.

(21) Appl. No.: 09/962,618

(22) Filed: Sep. 26, 2001

(65) Prior Publication Data

US 2002/0103357 A1  Aug. 1, 2002

(30) Foreign Application Priority Data

Sep. 26, 2000  (DE)  ............... 100 47 404

(51) Int. Cl.
C12P 13/04 (2006.01)
C12P 13/10 (2006.01)
C12N 15/00 (2006.01)
C12N 1/20 (2006.01)
C07H 21/02 (2006.01)
C07K 1/00 (2006.01)

(52) U.S. Cl. ............... 435/106; 435/115; 435/320.1; 435/252.32; 435/252.33; 536/23.1; 536/23.7; 530/350

(58) Field of Classification Search ............... 536/23.1, 536/23.2, 23.7, 24.3, 24.32, 24.33; 435/252.32, 435/320.1, 252.33, 106, 115
See application file for complete search history.

(56) References Cited

U.S. PATENT DOCUMENTS 6,962,989 B1 * 11/2005 Pompejus et al. ......... 536/23.7
7,160,711 B2 * 1/2007 Bathe et al. ............. 435/252.3
2002/0197605 A1 * 12/2002 Nakagawa et al. ............ 435/6

FOREIGN PATENT DOCUMENTS

EP       1 108 790 A2   6/2001
WO    WO 01/00843   *   1/2001

OTHER PUBLICATIONS

Branden et al. "Introduction to Protein Structure", Garland Publishing Inc., New York, 1991, p. 247.*
Witkowski et al. (1999) Biochemistry 38:11643-11650.*
"Stedman's Online Dictionary" definition of "protein" at 216.251.232.159/semdweb/internetsomd/ASP/1556547.asp, last visited Nov. 3, 2006.*
GenBank Accession No. AX120892, May 2001.*
A. Schlösser, et al., "The Streptomyces ATP-Binding Component MsiK Assists in Cellobiose and Maltose Transport," Journal of Bacteriology, vol. 179, No. 6, Mar. 1997, pp. 2092-2095.

* cited by examiner

Primary Examiner—David J. Steadman
(74) Attorney, Agent, or Firm—Smith, Gambrell & Russell, LLP

(57) ABSTRACT

The invention relates to an isolated polynucleotide from *Corynebacterium glutamicum* having a polynucleotide sequence which encodes the sugar import protein K (msiK) gene, and a host-vector system having a coryneform host bacterium in which the msiK gene is present in enhanced form and a vector which carries at least the msiK gene according to SEQ ID No 1, and the use of polynucleotides which comprise the sequences according to the invention as hybridization probes.

10 Claims, No Drawings

SEQUENCE LISTING

```
<160> NUMBER OF SEQ ID NOS: 2

<210> SEQ ID NO 1
<211> LENGTH: 1439
<212> TYPE: DNA
<213> ORGANISM: Corynebacterium glutamicum
<220> FEATURE:
<221> NAME/KEY: CDS
<222> LOCATION: (239)..(1234)
<223> OTHER INFORMATION:

<400> SEQUENCE: 1
gtgagcagaa cggtccagtg gtgaaggctt tcgggatcga caagaaggag gagcactccg      60
ccgatgagct caaataagcc gttgagtcct ttgagcttga tgccgcccca aaagagttgt     120
tgccaccgat cgcgaacttt ggcagtagcc atgcgttctg ctcctgacct tgaacagcgg     180
tcccaattta gacccgctaa acccacaatg tgtactggtg ctggtaattt agtagaac       238 atg gca acg gtc aca ttc gac aag gtc aca atc cgg tac ccc ggc gcg      286
Met Ala Thr Val Thr Phe Asp Lys Val Thr Ile Arg Tyr Pro Gly Ala
1               5                   10                  15 gag cgc gca aca gtt cat gag ctt gat tta gat atc gct gat ggc gag      334
Glu Arg Ala Thr Val His Glu Leu Asp Leu Asp Ile Ala Asp Gly Glu
                20                  25                  30 ttt ttg gtg ctc gtc ggc cct tcg ggt tgt ggt aaa tcc act acg ctg      382
Phe Leu Val Leu Val Gly Pro Ser Gly Cys Gly Lys Ser Thr Thr Leu
            35                  40                  45 cgt gct ttg gcg ggg ctt gag ggc gtg gag tcg ggt gtg atc aaa att      430
Arg Ala Leu Ala Gly Leu Glu Gly Val Glu Ser Gly Val Ile Lys Ile
        50                  55                  60 gat ggc aag gat gtc act ggt cag gag ccg gcg gat cgc gat atc gcg      478
Asp Gly Lys Asp Val Thr Gly Gln Glu Pro Ala Asp Arg Asp Ile Ala
65                  70                  75                  80 atg gtg ttc cag aat tat gct ctg tac cct cac atg acg gtg gcg aag      526
Met Val Phe Gln Asn Tyr Ala Leu Tyr Pro His Met Thr Val Ala Lys
                85                  90                  95 aat atg ggt ttt gcg ctg aag ttg gct aag ctg ccg cag gcg cag atc      574
Asn Met Gly Phe Ala Leu Lys Leu Ala Lys Leu Pro Gln Ala Gln Ile
            100                 105                 110 gat gcg aag gtc aat gag gct gcg gaa att ctt ggg ttg acg gag ttt      622
Asp Ala Lys Val Asn Glu Ala Ala Glu Ile Leu Gly Leu Thr Glu Phe
        115                 120                 125 ttg gat cgc aag cct aag gat tta tcg ggt ggt cag cgt cag cgt gtg      670
Leu Asp Arg Lys Pro Lys Asp Leu Ser Gly Gly Gln Arg Gln Arg Val
```

-continued

| | | | | | | | | | | | | | | | |
|---|---|---|---|---|---|---|---|---|---|---|---|---|---|---|---|
| gcg | atg | ggt | cgc | gcg | ttg | gtg | cgt | gat | ccg | aag | gtg | ttc | ctc | atg | gat | 718 |
| Ala | Met | Gly | Arg | Ala | Leu | Val | Arg | Asp | Pro | Lys | Val | Phe | Leu | Met | Asp |
| 145 | | | | 150 | | | | | 155 | | | | | 160 | |

| gag | ccg | ctg | tcc | aac | ctg | gat | gcg | aaa | ttg | cgc | gtg | caa | acc | cgc | gcg | 766 |
| Glu | Pro | Leu | Ser | Asn | Leu | Asp | Ala | Lys | Leu | Arg | Val | Gln | Thr | Arg | Ala |
| | | | | 165 | | | | | 170 | | | | | 175 | |

| gag | gtc | gct | gct | ttg | cag | cgt | cgc | ctg | ggc | acc | acc | acg | gtg | tat | gtc | 814 |
| Glu | Val | Ala | Ala | Leu | Gln | Arg | Arg | Leu | Gly | Thr | Thr | Thr | Val | Tyr | Val |
| | | | 180 | | | | | 185 | | | | | 190 | | |

| acc | cac | gat | cag | gtt | gag | gca | atg | acg | atg | ggc | gat | cgg | gtt | gcg | gtg | 862 |
| Thr | His | Asp | Gln | Val | Glu | Ala | Met | Thr | Met | Gly | Asp | Arg | Val | Ala | Val |
| | | | 195 | | | | | 200 | | | | | 205 | | |

| ctc | aag | gac | ggg | ttg | ctg | cag | cag | gtc | gca | ccg | ccc | agg | gag | ctt | tac | 910 |
| Leu | Lys | Asp | Gly | Leu | Leu | Gln | Gln | Val | Ala | Pro | Pro | Arg | Glu | Leu | Tyr |
| | 210 | | | | | 215 | | | | | 220 | | | | |

| gac | gcc | ccg | gtc | aac | gaa | ttc | gtt | gcg | ggc | ttc | atc | ggc | tcg | ccg | tcc | 958 |
| Asp | Ala | Pro | Val | Asn | Glu | Phe | Val | Ala | Gly | Phe | Ile | Gly | Ser | Pro | Ser |
| 225 | | | | | 230 | | | | | 235 | | | | | 240 |

| atg | aac | ctc | ttc | cct | gcc | aac | ggg | cac | aag | atg | ggt | gtg | cgc | ccg | gag | 1006 |
| Met | Asn | Leu | Phe | Pro | Ala | Asn | Gly | His | Lys | Met | Gly | Val | Arg | Pro | Glu |
| | | | | 245 | | | | | 250 | | | | | 255 | |

| aag | atg | ctg | gtc | aat | gag | acc | cct | gag | ggt | ttc | aca | agc | att | gat | gct | 1054 |
| Lys | Met | Leu | Val | Asn | Glu | Thr | Pro | Glu | Gly | Phe | Thr | Ser | Ile | Asp | Ala |
| | | | 260 | | | | | 265 | | | | | 270 | | |

| gtg | gtg | gat | atc | gtc | gag | gag | ctt | ggc | tcc | gaa | tcg | tat | gtt | tat | gcc | 1102 |
| Val | Val | Asp | Ile | Val | Glu | Glu | Leu | Gly | Ser | Glu | Ser | Tyr | Val | Tyr | Ala |
| | | | 275 | | | | | 280 | | | | | 285 | | |

| act | tgg | gag | ggc | cac | cgc | ctg | gtg | gcc | cgt | tgg | gtg | gaa | ggc | ccc | gtg | 1150 |
| Thr | Trp | Glu | Gly | His | Arg | Leu | Val | Ala | Arg | Trp | Val | Glu | Gly | Pro | Val |
| | 290 | | | | | 295 | | | | | 300 | | | | |

| cca | gcc | cct | ggc | acg | cct | gtg | act | ttt | tcc | tat | gat | gcg | gcg | cag | gcg | 1198 |
| Pro | Ala | Pro | Gly | Thr | Pro | Val | Thr | Phe | Ser | Tyr | Asp | Ala | Ala | Gln | Ala |
| 305 | | | | | 310 | | | | | 315 | | | | | 320 |

| cat | cat | ttc | gat | ctg | gag | tcg | ggc | gag | cgt | atc | gct | tagtttcgga | | | | 1244 |
| His | His | Phe | Asp | Leu | Glu | Ser | Gly | Glu | Arg | Ile | Ala | | | | |
| | | | | 325 | | | | | 330 | | | | | | | cgtggggagg cgtcgaaaag catctttatt tttgaccctc cggggtgat ttaacctaaa 1304 attccacaca aacgtgttcg aggtcattag attgataagc atctgttgtt aagaaaggtg 1364 acttcctatg tcctcgattt cccgcaagac cggcgcgtca cttgcagcca ccacactgtt 1424 ggcagcgatc gcact 1439

<210> SEQ ID NO 2
<211> LENGTH: 332
<212> TYPE: PRT
<213> ORGANISM: Corynebacterium glutamicum

<400> SEQUENCE: 2

Met Ala Thr Val Thr Phe Asp Lys Val Thr Ile Arg Tyr Pro Gly Ala
1               5                   10                  15

Glu Arg Ala Thr Val His Glu Leu Asp Leu Asp Ile Ala Asp Gly Glu
            20                  25                  30

Phe Leu Val Leu Val Gly Pro Ser Gly Cys Gly Lys Ser Thr Thr Leu
        35                  40                  45

Arg Ala Leu Ala Gly Leu Glu Gly Val Glu Ser Gly Val Ile Lys Ile
    50                  55                  60

Asp Gly Lys Asp Val Thr Gly Gln Glu Pro Ala Asp Arg Asp Ile Ala

-continued

```
65                  70                  75                  80
Met Val Phe Gln Asn Tyr Ala Leu Tyr Pro His Met Thr Val Ala Lys
                85                  90                  95

Asn Met Gly Phe Ala Leu Lys Leu Ala Lys Leu Pro Gln Ala Gln Ile
                100                 105                 110

Asp Ala Lys Val Asn Glu Ala Ala Glu Ile Leu Gly Leu Thr Glu Phe
                115                 120                 125

Leu Asp Arg Lys Pro Lys Asp Leu Ser Gly Gly Gln Arg Gln Arg Val
        130                 135                 140

Ala Met Gly Arg Ala Leu Val Arg Asp Pro Lys Val Phe Leu Met Asp
145                 150                 155                 160

Glu Pro Leu Ser Asn Leu Asp Ala Lys Leu Arg Val Gln Thr Arg Ala
                165                 170                 175

Glu Val Ala Ala Leu Gln Arg Arg Leu Gly Thr Thr Thr Val Tyr Val
                180                 185                 190

Thr His Asp Gln Val Glu Ala Met Thr Met Gly Asp Arg Val Ala Val
        195                 200                 205

Leu Lys Asp Gly Leu Leu Gln Gln Val Ala Pro Pro Arg Glu Leu Tyr
        210                 215                 220

Asp Ala Pro Val Asn Glu Phe Val Ala Gly Phe Ile Gly Ser Pro Ser
225                 230                 235                 240

Met Asn Leu Phe Pro Ala Asn Gly His Lys Met Gly Val Arg Pro Glu
                245                 250                 255

Lys Met Leu Val Asn Glu Thr Pro Glu Gly Phe Thr Ser Ile Asp Ala
                260                 265                 270

Val Val Asp Ile Val Glu Glu Leu Gly Ser Glu Ser Tyr Val Tyr Ala
        275                 280                 285

Thr Trp Glu Gly His Arg Leu Val Ala Arg Trp Val Glu Gly Pro Val
        290                 295                 300

Pro Ala Pro Gly Thr Pro Val Thr Phe Ser Tyr Asp Ala Ala Gln Ala
305                 310                 315                 320

His His Phe Asp Leu Glu Ser Gly Glu Arg Ile Ala
                325                 330
```

NUCLEOTIDE SEQUENCES WHICH CODE FOR THE MSIK GENE

BACKGROUND OF THE INVENTION

The invention provides nucleotide sequences from coryneform bacteria which code for the msiK gene and a process for the fermentative preparation of amino acids using bacteria in which the endogenous msiK gene is enhanced. All references cited herein are expressly incorporated by reference. Incorporation by reference is also designated by the term "I.B.R." following any citation.

L-Amino acids, in particular L-lysine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Methods of the recombinant DNA technique have also been employed for some years for improving the strain of *Corynebacterium* strains which produce L-amino acid, by amplifying individual amino acid biosynthesis genes and investigating the effect on the amino acid production.

The invention provides new measures for improved fermentative preparation of amino acids.

BRIEF SUMMARY OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine are mentioned in the following, not only the bases but also the salts, such as e.g. lysine monohydrochloride or lysine sulfate, are meant by this.

The invention provides an isolated polynucleotide from coryneform bacteria, comprising a polynucleotide sequence which codes for the msiK gene, chosen from the group consisting of
a) polynucleotide which is identical to the extent of at least 70% to a polynucleotide which codes for a polypeptide which comprises the amino acid sequence of SEQ ID No. 2,
b) polynucleotide which codes for a polypeptide which comprises an amino acid sequence which is identical to the extent of at least 70% to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c), the polypeptide preferably having the activity of the sugar import protein MsiK.

The invention also provides the above-mentioned polynucleotide, this preferably being a DNA which is capable of replication, comprising:
(i) the nucleotide sequence shown in SEQ ID No. 1, or
(ii) at least one sequence which corresponds to sequence (i) within the range of the degeneration of the genetic code, or
(iii) at least one sequence which hybridizes with the sequence complementary to sequence (i) or (ii), and optionally
(iv) sense mutations of neutral function in (i).

The invention also provides
a polynucleotide, in particular DNA, which is capable of replication and comprises the nucleotide sequence as shown in SEQ ID No. 1;
a polynucleotide which codes for a polypeptide which comprises the amino acid sequence as shown in SEQ ID No. 2;
a vector containing the polynucleotide according to the invention, in particular a shuttle vector or plasmid vector, and
coryneform bacteria which contain the vector or in which the endogenous msiK gene is enhanced.

The invention also provides polynucleotides, which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No.1 or a fragment thereof, and isolation of the polynucleotide sequence mentioned.

DETAILED DESCRIPTION OF THE INVENTION

Polynucleotides which comprise the sequences according to the invention are suitable as hybridization probes for RNA, cDNA and DNA, in order to isolate, in the full length, nucleic acids or polynucleotides or genes which code for the sugar import protein MsiK or to isolate those nucleic acids or polynucleotides or genes which have a high similarity of sequence with that of the msiK gene. They can also be attached as a probe to so-called "arrays", "micro arrays" or "DNA chips" in order to detect and to determine the corresponding polynucleotides or sequences derived therefrom, such as e.g. RNA or cDNA.

Polynucleotides which comprise the sequences according to the invention are furthermore suitable as primers with the aid of which DNA of genes which code for the sugar import protein MsiK can be prepared by the polymerase chain reaction (PCR).

Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least in particular 70% to 80%, preferably at least 81% to 85%, particularly preferably at least 86% to 90%, and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the sugar import protein MsiK and also those which are at least 70% to 80%, preferably at least 81% to 85%, particularly preferably at least 86% to 90%, and very particularly preferably at least 91%, 93%, 95%, 97% or 99% identical to the polypeptide according to SEQ ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the msiK gene are enhanced, in particular over-expressed.

The term "enhancement" in this connection describes the increase in the intracellular activity of one or more enzymes (proteins) in a microorganism which are coded by the corresponding DNA, for example by increasing the number of copies of the gene or allele or of the genes or alleles, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The microorganisms which the present invention provides can produce L-amino acids from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains
*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-amino acid-producing mutants or strains prepared therefrom.

The new msiK gene from *C. glutamicum* which codes for the sugar import protein MsiK has been isolated.

To isolate the msiK gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990) I.B.R., or the handbook by Sambrook et al.: Molecular Cloning, A Laboratory Manual (Cold Spring Harbor Laboratory Press, 1989) I.B.R. may be mentioned as an example. A well-known gene library is that of the *E. coli* K-12 strain W3110 set up in λ vectors by Kohara et al. (Cell 50, 495-508 (1987)) I.B.R. Bathe et al. (Molecular and General Genetics, 252:255-265, 1996) I.B.R. describe a gene library of *C. glutamicum* ATCC13032, which was set up with the aid of the cosmid vector SuperCos I (Wahl et al., 1987, Proceedings of the National Academy of Sciences USA, 84:2160-2164) I.B.R. in the *E. coli* K-12 strain NM554 (Raleigh et al., 1988, Nucleic Acids Research 16:1563-1575) I.B.R.

Börmann et al. (Molecular Microbiology 6(3), 317-326) (1992)) I.B.R. in turn describe a gene library of *C. glutamicum* ATCC13032 using the cosmid pHC79 (Hohn and Collins, Gene 11, 291-298 (1980) I.B.R.).

To prepare a gene library of *C. glutamicum* in *E. coli* it is also possible to use plasmids such as pBR322 (Bolivar, Life Sciences, 25, 807-818 (1979) I.B.R.) or pUC9 (Vieira et al., 1982, Gene, 19:259-268 I.B.R.). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645-4649) I.B.R. The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463-5467, 1977) I.B.R.

The resulting DNA sequences can then be investigated with known algorithms or sequence analysis programs, such as e.g. that of Staden (Nucleic Acids Research 14, 217-232 (1986)) I.B.R., that of Marck (Nucleic Acids Research 16, 1829-1836 (1988)) I.B.R. or the GCG program of Butler (Methods of Biochemical Analysis 39, 74-97 (1998)) I.B.R.

The new DNA sequence of *C. glutamicum* which codes for the msiK gene and which, as SEQ ID No. 1, is a constituent of the present invention has been found. The amino acid sequence of the corresponding protein has furthermore been derived from the present DNA sequence by the methods described above. The resulting amino acid sequence of the msiK gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751-757 (1987)) I.B.R., in O'Regan et al. (Gene 77:237-251 (1989)) I.B.R., in Sahin-Toth et al. (Protein Sciences 3:240-247 (1994)) I.B.R., in Hochuli et al. (Bio/Technology 6:1321-1325 (1988)) I.B.R. and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255-260) I.B.R. The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996 I.B.R.).

A 5×SSC buffer at a temperature of approx. 50° C.-68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995 I.B.R.) a temperature of approx. 50° C.-68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approx. 1-2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994) I.B.R.

It has been found that coryneform bacteria produce amino acids in an improved manner after over-expression of the msiK gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137-146 (1987)) I.B.R., in Guerrero et al. (Gene 138, 35-41 (1994)) I.B.R., Tsuchiya and Morinaga (Bio/Technology 6, 428-430 (1988)) I.B.R., in Eikmanns et al. (Gene 102, 93-98 (1991)) I.B.R., in EP 0 472 869 I.B.R., in US 4,601,893 I.B.R., in Schwarzer and Pühler (Bio/Technology 9, 84-87 (1991) I.B.R., in Reinscheid et al. (Applied and Environmental Microbiology 60, 126-132 (1994)) I.B.R., in LaBarre et al. (Journal of Bacteriology 175, 1001-1007 (1993)) I.B.R., in WO 96/15246 I.B.R., in Malumbres et al. (Gene 134, 15-24 (1993)) I.B.R., in JP-A-10-229891 I.B.R., in Jensen and Hammer (Biotechnology and Bioengineering 58, 191-195 (1998)) I.B.R., in Makrides (Microbiological Reviews 60:512-538 (1996)) I.B.R. and in known textbooks of genetics and molecular biology.

By way of example, for enhancement the msiK gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549-554 I.B.R.), pEKEx1 (Eikmanns et al., I.B.R. Gene 102:93-98 (1991)) or pHS2-1 (Sonnen et al., Gene 107:69-74 (1991) I.B.R.) are based on the cryptic plasmids pHM1519, pBL1 or pGA1. Other plasmid vectors, such as e.g. those based on pCG4 (U.S. Pat. No. 4,489,160 I.B.R.), or pNG2 (Serwold-Davis et al., FEMS Microbiology Letters 66, 119-124 (1990) I.B.R.), or pAG1 (U.S. Pat. No. 5,158,891 I.B.R.), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126-132 (1994)) I.B.R. for duplication or amplification of the hom-thrB operon. In this method, the complete gene is cloned in a plasmid vector which can replicate in a host (typically *E. coli*), but not in *C. glutamicum*. Possible vectors are, for example, psUP301 (Simon et al., Bio/Technology 1, 784-791 (1983) I.B.R. I.B.R.), pK18mob or pK19mob (Schäfer et al., Gene 145, 69-73 (1994) I.B.R.), pGEM-T (Promega Corporation, Madison, Wis., USA), pCR2.1-TOPO (Shuman (1994). Journal of Biological Chemistry 269:32678-84 I.B.R.; U.S. Pat. No. 5,487,993 I.B.R.), pCR®Blunt (Invitrogen, Groningen, Holland; Bernard et al., Journal of Molecular Biology, 234: 534-541 (1993)) I.B.R., pEM1 (Schrumpf et al, 1991, Journal of Bacteriology 173:4510-4516 I.B.R.) or pBGS8 (Spratt et al., 1986, Gene 41: 337-342 I.B.R.). The plasmid vector which contains the gene to be amplified is then transferred into the desired strain of *C. glutamicum* by conjugation or transformation. The method of conjugation is described, for example, by Schafer et al. (Applied and Environmental Microbiology 60, 756-759 (1994)) I.B.R. Methods for transformation are described, for example, by Thierbach et al. (Applied Microbiology and Biotechnology 29, 356-362 (1988)) I.B.R., Dunican and Shivnan (Bio/Technology 7, 1067-1070 (1989)) I.B.R. and Tauch et al. (FEMS Microbiological Letters 123, 343-347 (1994)) I.B.R. After homologous recombination by means of a "cross over" event, the resulting strain contains at least two copies of the gene in question.

In addition, it may be advantageous for the production of L-amino acids to enhance, in particular overexpress one or more enzymes of the particular biosynthesis pathway, of glycolysis, of anaplerosis, of the citric acid cycle, of the pentose phosphate cycle, of amino acid export and optionally regulatory proteins, in addition to the msiK gene.

Thus, for the preparation of L-amino acids, in addition to enhancement of the msiK gene, one or more endogenous genes chosen from the group consisting of
the dapA gene which codes for dihydrodipicolinate synthase (EP-B 0 197 335 I.B.R.),
the gap gene which codes for glyceraldehyde 3-phosphate dehydrogenase (Eikmanns (1992), Journal of Bacteriology 174:6076-6086 I.B.R.),
the tpi gene which codes for triose phosphate isomerase (Eikmanns (1992), Journal of Bacteriology 174:6076-6086
the pgk gene which codes for 3-phosphoglycerate kinase (Eikmanns (1992), Journal of Bacteriology 174:6076-6086 I.B.R.),
the zwf gene which codes for glucose 6-phosphate dehydrogenase (JP-A-09224661 I.B.R.),
the pyc gene which codes for pyruvate carboxylase (DE-A-198 31 609 I.B.R.),
the mqo gene which codes for malate-quinone oxidoreductase (Molenaar et al., European Journal of Biochemistry 254, 395-403 (1998) I.B.R.),
the lysC gene which codes for a feed-back resistant aspartate kinase (Accession No.P26512; EP-B-0387527 I.B.R.; EP-A-0699759 I.B.R.),
the lysE gene which codes for lysine export (DE-A-195 48 222 I.B.R.),
the hom gene which codes for homoserine dehydrogenase (EP-A 0131171 I.B.R.),
the ilvA gene which codes for threonine dehydratase (Mockel et al., Journal of Bacteriology (1992) 8065-8072) I.B.R.) or the ilvA(Fbr) allele which codes for a "feed back resistant" threonine dehydratase (Möckel et al., (1994) Molecular Microbiology 13: 833-842 I.B.R.),
the ilvBN gene which codes for acetohydroxy-acid synthase (EP-B 0356739 I.B.R.),
the ilvD gene which codes for dihydroxy-acid dehydratase (Sahm and Eggeling (1999) Applied and Environmental Microbiology 65: 1973-1979 I.B.R.),
the zwa1 gene which codes for the Zwa1 protein (DE: 19959328.0 I.B.R., DSM 13115), can be enhanced, in particular over-expressed.

It may furthermore be advantageous for the production of L-amino acids, in addition to the enhancement of the msiK gene, for one or more genes chosen from the group consisting of:
the pck gene which codes for phosphoenol pyruvate carboxykinase (DE 199 50 409.1 I.B.R.; DSM 13047),
the pgi gene which codes for glucose 6-phosphate isomerase (U.S. Pat. No. 6,586,214 I.B.R.; DSM 12969),
the poxB gene which codes for pyruvate oxidase (DE: 1995 1975.7 I.B.R.; DSM 13114),
the zwa2 gene which codes for the Zwa2 protein (DE: 19959327.2 I.B.R., DSM 13113)
to be attenuated, in particular for the expression thereof to be reduced.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

In addition to over-expression of the msiK gene it may furthermore be advantageous for the production of amino acids to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982) I.B.R.

The invention also provides the microorganisms prepared according to the invention, and these can be cultured continuously or discontinuously in the batch process (batch culture) or in the fed batch (feed process) or repeated fed batch process (repetitive feed process) for the purpose of production of amino acids. A summary of known culture methods is described in the textbook by Chmiel (Bioprozesstechnik 1. Einfuhrung in die Bioverfahrenstechnik [Bioprocess Technology 1. Introduction to Bioprocess Technology] (Gustav Fischer Verlag, Stuttgart, 1991)) I.B.R. or in the textbook by Storhas (Bioreaktoren und periphere Einrichtungen [Bioreactors and Peripheral Equipment] (Vieweg Verlag, Braunschweig/Wiesbaden, 1994)) I.B.R.

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981) I.B.R.

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190 I.B.R.) by ion exchange chromatography with subsequent ninhydrin derivation, or it can be carried out by reversed phase HPLC, for example as described by Lindroth et al. (Analytical Chemistry (1979) 51: 1167-1174) I.B.R.

The process according to the invention is used for fermentative preparation of amino acids.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, NY, USA) I.B.R. Methods for transformation of *Escherichia coli* are also described in this handbook.

The composition of the usual nutrient media, such as LB or TY medium, can also be found in the handbook by Sambrook et al.

EXAMPLE 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168-179) I.B.R. and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector Super-Cos1 (Wahl et al. (1987) Proceedings of the National Academy of Sciences USA 84:2160-2164 I.B.R.), obtained from Stratagene (La Jolla, USA, Product Description Super-Cos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04 I.B.R.). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04 I.B.R.). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acids Research 16:1563-1575 I.B.R.) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor) I.B.R., the cells being plated out on LB agar (Lennox, 1955, Virology, 1:190 I.B.R.) with 100 mg/l ampicillin. After incubation overnight at 37° C., recombinant individual clones were selected.

EXAMPLE 2

Isolation and Sequencing of the msiK Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), was cleaved with the restriction enzyme BamHI (Amersham Pharmacia, Freiburg, Germany, Product Description BamHI, Product No. 27-0868-04). The ligation of the cosmid fragments in the sequencing vector pzero-1 was carried out as described by Sambrook et al. (1989, Molecular Cloning: A Laboratory Manual, Cold Spring Harbor) I.B.R., the DNA mixture being incubated overnight with T4 ligase (Pharmacia Biotech, Freiburg, Germany). This ligation mixture was then electroporated (Tauch et al. 1994, FEMS Microbiol Letters, 123:343-7 I.B.R.) into the *E. coli* strain DH5αMCR (Grant, 1990, Proceedings of the National Academy of Sciences U.S.A., 87:4645-4649 I.B.R.) and plated out on LB agar (Lennox, 1955, Virology, 1:190 I.B.R.) with 50 mg/l zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463-5467) I.B.R. with modifications according to Zimmermann et al. (1990, Nucleic Acids Research, 18:1067) I.B.R. The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" 1 sequencer from PE Applied Biosystems (Weiterstadt, Germany).

The raw sequence data obtained were then processed using the Staden program package (1986, Nucleic Acids Research, 14:217-231 I.B.R.) version 97-0. The individual sequences of the pzerol derivatives were assembled to a continuous contig. The computer-assisted coding region analysis was prepared with the XNIP program (Staden, 1986, Nucleic Acids Research, 14:217-231 I.B.R.). Further analyses can be carried out with the "BLAST search program" (Altschul et al., 1997, Nucleic Acids Research, 25:3389-3402 I.B.R.) against the non-redundant databank of the "National Center for Biotechnology Information" (NCBI, Bethesda, Md., USA) I.B.R.

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R.

The resulting nucleotide sequence is shown in SEQ ID No. 1. Analysis of the nucleotide sequence showed an open reading frame of 999 base pairs, which was called the msiK gene. The msiK gene codes for a protein of 332 amino acids.

This application claims priority to German Priority Document Application No. 100 47 404.7, filed on Sep. 26, 2000. The above German Priority Document is hereby incorporated by reference in its entirety.

We claim:

1. An isolated polynucleotide comprising the nucleotide sequence of SEQ ID NO: 1.

2. An isolated polynucleotide comprising the nucleotide sequence of the complete complement of SEQ ID NO: 1.

3. A vector comprising the isolated polynucleotide selected from the group consisting of:
   an isolated polynucleotide comprising the nucleotide sequence of SEQ ID NO: 1; and
   an isolated polynucleotide comprising the nucleotide sequence of the complete complement of SEQ ID NO: 1.

4. A recombinant host cell of the genus *Corynebacterium* transformed with the isolated polynucleotide selected from the group consisting of:
   an isolated polynucleotide comprising the nucleotide sequence of SEQ ID NO: 1; and
   an isolated polynucleotide comprising the nucleotide sequence of the complete complement of SEQ ID NO: 1.

5. The host cell of claim 4, wherein said host cell is of the species *Corynebacterium glutamicum*.

6. A recombinant host cell of the genus *Corynebacterium* or of the species *Escherichia coli* comprising the vector of claim 3.

7. The host cell of claim 6, wherein said host cell is of the species *Corynebacterium glutamicum*.

8. A method for producing an L-amino acid which comprises
   culturing in a medium suitable for producing the L-amino acid a recombinant host cell of the genus *Corynebacterium* transformed with
   an isolated polynucleotide comprising the nucleotide sequence of SEQ ID NO: 1.

9. The method of claim 8, wherein the host cell is of the species *Corynebacterium glutamicum*.

10. The method of claim 8, wherein the L-amino acid is L-Lysine.

* * * * *